United States Patent
Igarashi

(10) Patent No.: US 6,898,022 B2
(45) Date of Patent: May 24, 2005

(54) STEREO OPTICAL SYSTEM PAIR FOR STEREO ENDOSCOPE SYSTEM

(75) Inventor: Tsutomu Igarashi, Hachioji (JP)

(73) Assignee: Olympus Corporation, Tokyo (JP)

( * ) Notice: Subject to any disclaimer, the term of this patent is extended or adjusted under 35 U.S.C. 154(b) by 315 days.

(21) Appl. No.: 10/177,260

(22) Filed: Jun. 20, 2002

(65) Prior Publication Data

US 2004/0002627 A1 Jan. 1, 2004

(51) Int. Cl.[7] .............................................. G02B 15/14
(52) U.S. Cl. ....................... 359/676; 359/432; 359/462; 600/111; 600/166; 600/168
(58) Field of Search ................... 359/676–677, 359/680–682, 684, 689–691, 419–423, 432–434, 462, 466; 348/65; 600/101, 109, 111, 117, 160, 162, 163, 165–168

(56) References Cited

U.S. PATENT DOCUMENTS

| | | | | |
|---|---|---|---|---|
| 4,976,522 A | * | 12/1990 | Igarashi | 359/680 |
| 5,577,991 A | * | 11/1996 | Akui et al. | 600/111 |
| 5,776,049 A | * | 7/1998 | Takahashi | 600/111 |
| 5,933,282 A | * | 8/1999 | Tomioka et al. | 359/685 |
| 6,433,937 B1 | * | 8/2002 | Konno | 359/682 |
| 6,618,205 B2 | * | 9/2003 | Murayama | 359/645 |

* cited by examiner

Primary Examiner—Jordan M. Schwartz
(74) Attorney, Agent, or Firm—Hogan & Hartson LLP

(57) ABSTRACT

An optical system pair for a stereo endoscope is described which enables adjustment of magnification matching in the production phase with low cost and small size for the resulting stereo endoscope products. The stereo optical system pair for stereo endoscope system includes a right optical system and a left optical system, wherein one of the right and left optical systems includes a lens group which has a refractive power, and which is designed to be moveable axially with a moveable range and has a position within the moveable range at which optical magnification equals to −1. Also described are optical arrangements of a stereo endoscope incorporating the stereo optical system pair.

28 Claims, 5 Drawing Sheets

ISP

OBSP

STEREO OPTICAL SYSTEM PAIR FOR STEREO ENDOSCOPE SYSTEM

BACKGROUND OF THE INVENTION

1. Field of the Invention

This invention relates to a stereo optical system pair for a stereo endoscope system which has right and left optical channels.

2. Description of the Related Art

The following references relate to optical system for stereo endoscopes: U.S. Pat. No. 5,527,263, U.S. Pat. No. 5,522,789, U.S. Pat. No. 5,577,991, U.S. Pat. No. 5,743,846, and Japanese Patent publication No. H6-59196. The following reference relates to optical system which enables adjustment of magnification for endoscopes: U.S. Pat. No. 4,976,522. The last five patents above are commonly assigned as the present application.

Endoscopic robot surgery system continues progressing remarkably. Since the robot surgery system enables highly precise treatment, an endoscope system for the robot surgery system is desired to have stereoscopic imaging and high image quality in order to give surgeons depth perception and detail structure information of an object being observed. It is very important to guarantee matching right and left images for stereo endoscope systems which have right and left optical channels. If a stereo endoscope system consist of endoscope components and camera head components, it is desirable that stereo matching quality of each of all the endoscope products and all the camera head products be guaranteed independently to maintain interchangeability between the components in the stereo endoscope system.

The following are basic optical properties regarding stereo matching, which is to be guaranteed for stereoscopic imaging in general: (A) magnification matching; (B) focus matching; (C) image X-Y shifting matching; and (D) image rotation matching.

Adjustment structures and methods of the matching properties depend on the framework of optical design. An issue to be considered initially in design procedure is how to obtain magnification matching. In order to satisfy magnification matching by adjustment in the assembling process, it is necessary that the right or left optical system be capable of varying magnification which is used to remove magnification difference between right and left channels. Furthermore, it is desired that focus position shift be as small as possible while magnification is varying, in order to reduce dependency of magnification matching adjustment on focus matching adjustment. Such dependency makes magnification measurement difficult in magnification adjustment process, and increases cycles of alternating magnification adjustment and focus adjustment.

In a structure using zoom optical units as shown in U.S. Pat. No. 5,522,789 for this purpose, production cost is likely higher and body size is likely larger because of existing cam mechanism of the zoom optical unit. In a structure having no magnification matching adjustment, as shown in U.S. Pat. No. 5,527,263, it is required to reduce manufacturing error of magnification in each optical channel sufficiently. In order to satisfy this requirement, all the optical and related mechanical components must be manufactured with higher precision than normally required. It is impossible or impractical to apply such requirement for all stereo endoscope systems which have various specifications and cost targets.

SUMMARY OF THE INVENTION

Accordingly, the present invention is directed to a stereo optical system pair for stereo endoscope system that substantially obviates one or more of the problems due to limitations and disadvantages of the related art.

A objective of this invention is to provide a simple optical system pair which enables adjustment of magnification matching in production phase with low cost and which results in a compact size for the stereo endoscope products.

Additional features and advantages of the invention will be set forth in the descriptions that follow and in part will be apparent from the description, or may be learned by practice of the invention. The objectives and other advantages of the invention will be realized and attained by the structure particularly pointed out in the written description and claims thereof as well as the appended drawings.

To achieve these and other advantages and in accordance with the purpose of the present invention, as embodied and broadly described, the present invention provides a stereo optical system pair for stereo endoscope system which includes a right optical system and a left optical system, wherein one of the right and the left optical system includes a lens group which has a refractive power, and which is moveable axially within a moveable range and has a position within the moveable range at which its optical magnification equals to −1.

It is to be understood that both the foregoing general description and the following detailed description are exemplary and explanatory and are intended to provide further explanation of the invention as claimed.

DETAILED DESCRIPTION OF THE PREFERRED EMBODIMENTS

In this disclosure, the following definitions are used in the technical explanation. A "stereo optical system pair" refers to a pair including a right optical system and a left optical system, both of which form or transfer respective images. A "front side" refers to a side of an optical system near the object to be observed, and a "rear side" refers to a side opposite to the "front side". A "far conjugation side" of an optical system refers to a side which is located at a relatively large distance (including infinity) from an image, and a "near conjugation side" refers to a side opposite to the "far conjugation side".

Figure 1:
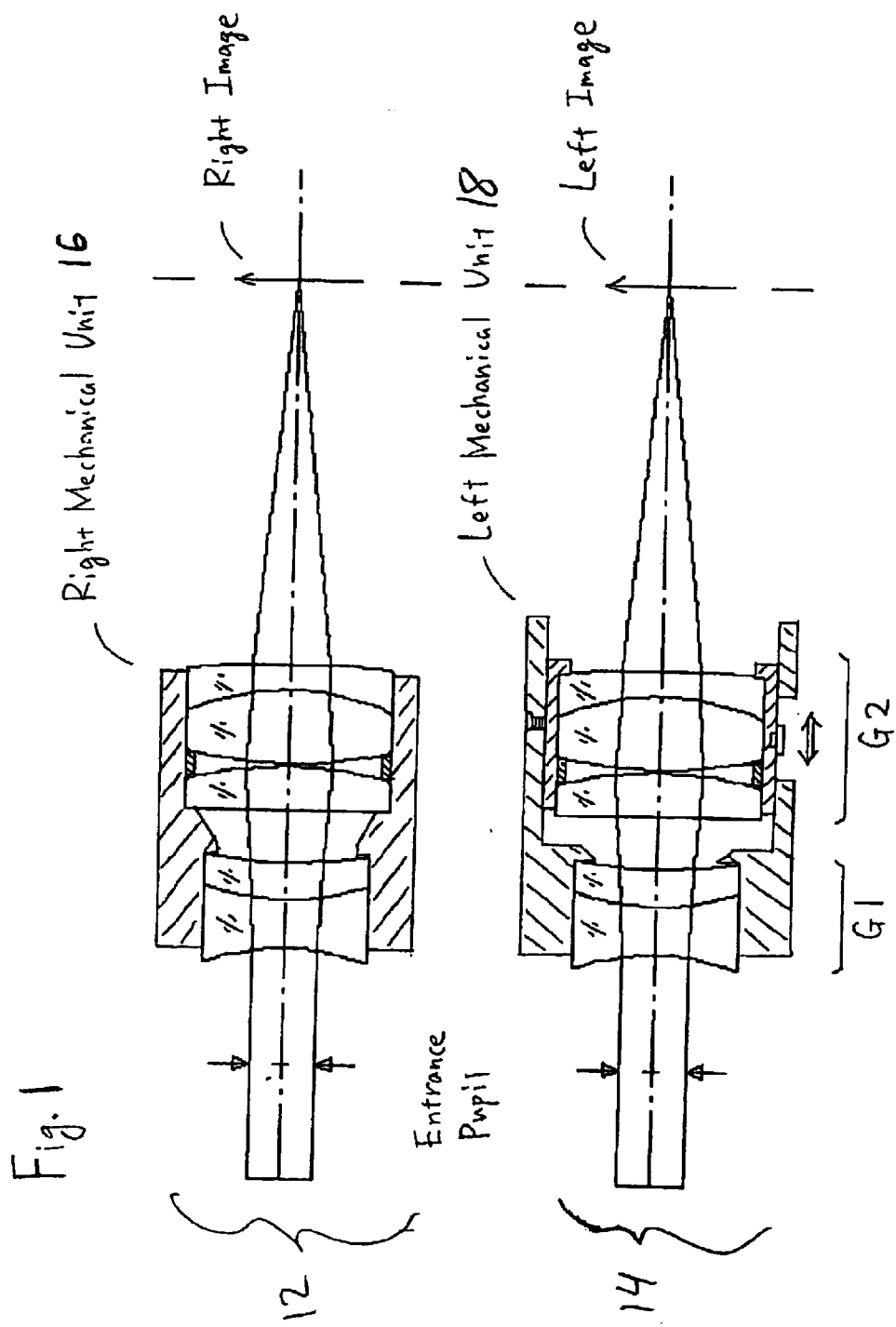
FIG. 1 is a diagram showing a stereo optical system pair according to a first embodiment of this invention.

A stereo endoscope system according to embodiments of this invention includes a stereo optical system pair designed according to principles of this invention. FIG. 1 shows a first structure of a stereo optical system pair for a stereo endoscope system according to an embodiment of the present invention. The first structure includes a right optical system 12 and a left optical system 14, wherein one of the right and left optical systems (in the example of FIG. 1, the left optical system) includes, in the order from the far conjugation side, a first lens group G1 which has negative refractive power, a second lens group G2 which has positive refractive power, and which is designed to be moveable axially and independently from the first lens group within a moveable range and has a position within the moveable range at which its optical magnification equals to −1. Such a structure enables adjustment of magnification matching of a stereo endoscope optical system with very small shifting of focus position, without using a cam mechanism as conventionally used in a zoom optical unit.

The second lens group G2 is implemented with a function of varying the magnification without a large shift of the focusing position. If the second lens group is moved to vary the total magnification of the optical system, the focus position of the optical system will be shifted according to following equation (1).

$$D2 = f2 * (2 - \beta 2 - 1/\beta 2) \qquad (1)$$

In equation (1), $\beta 2$ is the optical magnification of the second lens group G2; f2 is the focal length of the second lens group; and D2 is the distance between the input image position and the output image position of the second lens group. The following data (Table 1) is calculated using equation (1).

TABLE 1

| $\beta 2$ | −0.80 | −0.85 | −0.90 | −0.95 | −1.00 | −1.05 | −1.10 | −1.15 | −1.20 |
|---|---|---|---|---|---|---|---|---|---|
| D2/f2 | 4.050 | 4.026 | 4.011 | 4.003 | 4.000 | 4.002 | 4.009 | 4.020 | 4.033 |

Since the input image position of the second lens group G2 is fixed by the first lens group G1 which is independent from the movement of the second lens group, changing of D2 means shifting of the focus position. As shown by the above data, if $\beta 2$ varies in the vicinity of −1, D2 varies only slightly around 4*f2 and as a result, the shift in focus position is small.

Since $\beta 2$ relates to the total magnification of the optical system, the moveable range of the second lens group G2 must be selected according to the required $\beta 2$ range. Furthermore, requirements of the $\beta 2$ range should be determined according to the magnification deviation of the whole optical system of a stereo endoscope product, which is caused by manufacturing error of components.

In the case of a stereo endoscope including a stereo objective optical system pair, the $\beta 2$ range is around ±10% because an objective optical system of an endoscope tends to have a large magnification deviation. In the case of a stereo endoscope including a stereo camera head, the $\beta 2$ range is around ±5% or less. Therefore, the maximum $\beta 2$ range for the purpose of this embodiment is assumed to be ±10%. The above data table (Table 1) shows that it is generally sufficient for the second lens group G2 to have a position within the moveable range at which $\beta 2$ equals to −1.

Since the movement of the second lens group G2 is independent from the first lens group G1, a large and complicated mechanical unit holding this optical system such as a cam mechanism of zoom optical unit is unnecessary.

The optical power layout of the optical system of FIG. 1 is generally known as a "retro-focus type". Therefore, the first structure described above is suitable in applications where a smaller focal length and a longer back focal distance on the near conjugation side are desired. For example, it is suitable for a stereo camera head employing a 3-chip CCD camera.

Figure 2:
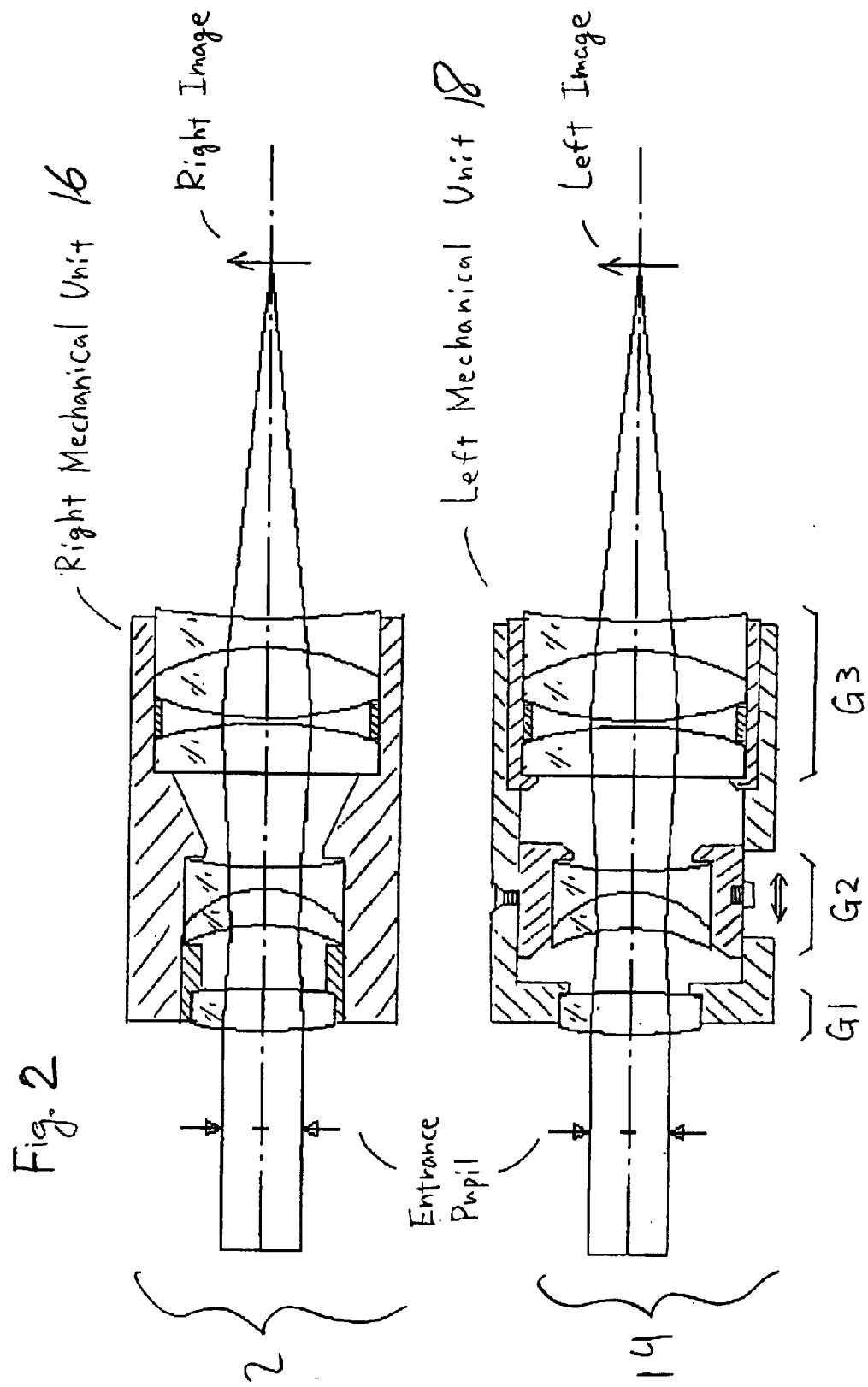
FIG. 2 is a diagram showing a stereo optical system pair according to a second embodiment of this invention.

FIG. 2 shows a second structure of a stereo optical system pair for stereo endoscope system according to another embodiment of the present invention. The second structure includes a right optical system 12 and a left optical system 14, wherein one of the right and left optical systems (in the example of FIG. 2, the left optical system) includes, in the order from the far conjugation side, a first lens group G1 which has a positive refractive power, a second lens group G2 which has a negative refractive power, and which is designed to be moveable axially independently from the other lens groups with a moveable range and has a position within the moveable range at which its optical magnification equals to −1, and a third lens group G3 which has a positive refractive power.

The second structure is based on the same optical principle as the first structure shown in FIG. 1. The equation (1) described earlier is applicable to the second structure because it is independent of the optical power of the moveable lens group. Since the movement of the second lens group is independent of the other lens groups, a cam mechanism is not necessary. The optical power layout of the optical system of FIG. 2 is generally known as a "triplet type". Since the optical power layout of the second structure (FIG. 2) is more optimal in total length than the first structure (FIG. 1), the second structure is generally more suitable in applications where a long focal length and a short total length are desired.

The first and the second structure shown in FIGS. 1 and 2 are generally based on the same optical principle. Therefore, the following basic structure includes common potions of the first and the second structures. A third structure of a stereo optical system pair for stereo endoscope system includes a right optical system and a left optical system, wherein one of the right and left optical systems includes a lens group which has refractive power, and which is designed to be moveable axially with a moveable range and has a position within the moveable range at which its optical magnification equals to −1.

Hereafter, design parameters and conditions common to the above three structures are explained. Preferably, the right optical system and the left optical system have the same optical design data in order to simplify the manufacturing process for the optical system components.

The design of the mechanical units that hold the stereo optical system pair depends on whether there are additional considerations other than magnification matching. If magnification matching is the only requirement in the magnification adjustment process, a right mechanical unit 16 (FIGS. 1 and 2) holding the right optical system and a left mechanical unit 18 holding the left optical system may be different. For example the right mechanical unit has adjustable structure and the left mechanical unit has no adjustable structure. If absolute magnification adjustment is additionally required in the process, both the right and the left mechanical units 16 and 18 preferably have an adjustable structure.

Hereafter, the stereo endoscope of this invention is explained based on examples. A first example relates to the first structure of a stereo optical system pair shown in FIG. 1. The optical data of the first example are as followings.

EXAMPLE 1

In Tables 2 and 3 below, the symbols have the following meanings:

SUR: Surface number
RAD: Radius [mm] THI: Thickness [mm]
Nd: refractive index (d-line)
Vd: abbe number (d-line)

TABLE 2

| SUR | RAD | THI | Nd | Vd |
|---|---|---|---|---|
| 1 | INF | 9.26 | AIR | |
| 2 | −13.703 | 3.24 | 1.48749 | 70.23 |
| 3 | 13.703 | 2.50 | 1.80610 | 40.92 |
| 4 | 25.201 | 3.45 | AIR | |
| 5 | INF | 3.00 | 1.77250 | 49.60 |
| 6 | −21.275 | 0.20 | AIR | |
| 7 | 24.055 | 4.94 | 1.72916 | 54.68 |
| 8 | −14.353 | 1.70 | 1.84666 | 23.78 |
| 9 | −79.774 | 25.79 | AIR | |
| 10 | INF | | | |

In this example, the following conditions are used:

Distance to object plane: Infinity
Surface number of aperture stop plane: 1
Surface number of image plane: 10
Image Height: 2.28 mm
Total focal length: 22.00 mm
F number: 5.5
First lens group: Surface No. 2 to 4
Second lens group: Surface No. 5 to 9
Magnification of second lens group ($\beta 2$): −1.00

Moveable range of second lens group (thickness of Surface No. 4):

| $\beta 2$ | −0.9 | −1.0 | −1.1 |
|---|---|---|---|
| THI(SUR = 4) | 5.09 | 3.45 | 2.11 |
| Focus shift | +0.17 | (base) | +0.14 |

In FIG. 1, the right and left optical systems 12 and 14 are held by a right and a left mechanical unit 16 and 18, respectively. Only the left mechanical unit 18 has a magnification adjustment structure. While magnification matching adjustment is carried out, the first lens group (G1) is fixed and the second lens group (G2) is moved to obtain magnification matching.

A second example related to the second structure of a stereo optical system pair shown in FIG. 2. The optical design data of the second example are as followings.

EXAMPLE 2

TABLE 3

| SUR | RAD | THI | Nd | Vd |
|---|---|---|---|---|
| 1 | INF | 5.94 | AIR | |
| 2 | 23.118 | 2.60 | 1.48749 | 70.23 |
| 3 | −55.761 | 3.99 | AIR | |
| 4 | −11.096 | 2.30 | 1.80518 | 25.42 |
| 5 | −6.486 | 1.30 | 1.60342 | 38.03 |
| 6 | 21.275 | 6.05 | AIR | |
| 7 | INF | 3.20 | 1.83400 | 37.16 |
| 8 | −21.479 | 0.30 | AIR | |
| 9 | 19.230 | 4.50 | 1.77250 | 49.60 |
| 10 | −13.947 | 1.80 | 1.80518 | 25.42 |
| 11 | 44.846 | 22.65 | AIR | |
| 12 | INF | | | |

In this example, the following conditions are used:

Distance to object plane: Infinity
Surface number of aperture stop plane: 1
Surface number of image plane: 12
Image Height: 3.1 mm
Total focal length: 24.92 mm
F number: 5.0
First lens group: Surface No. 2 to 3
Second lens group: Surface No. 4 to 6
Third lens group: Surface No. 7 to 11
Magnification of second lens group ($\beta 2$): −1.00

Moveable range of second lens group:

| $\beta 2$ | −0.9 | −1.0 | −1.1 |
|---|---|---|---|
| THI(SUR = 3) | 2.41 | 3.99 | 5.28 |
| THI(SUR = 6) | 7.63 | 6.05 | 4.76 |
| Focus shift | −0.08 | (base) | −0.07 |

In FIG. 2, the right and left optical systems 12 and 14 are held by a right and a left mechanical unit 16 and 18, respectively. Only the left mechanical unit 18 has a magnification adjustment structure. While magnification matching adjustment is carried out, the first lens group (G1) and the third lens group (G3) are fixed and the second lens group (G2) is moved to obtain magnification matching.

Figure 3:
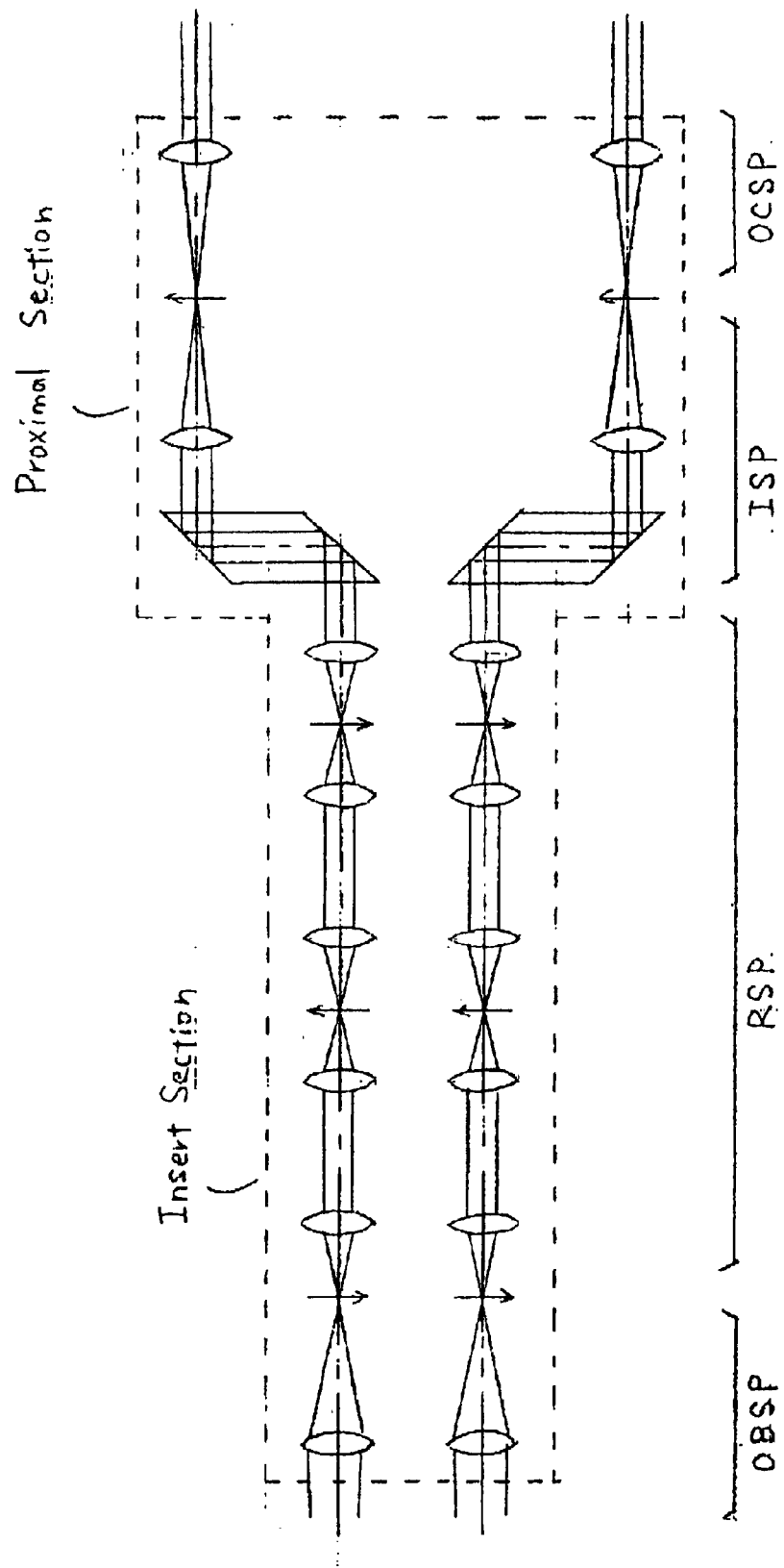
FIG. 3 is a diagram showing an arrangement of a stereo optical system pair according to an embodiment of this invention in a stereo endoscope to be connected to a stereo camera head.

Hereafter, a system incorporating the stereo optical system pair for stereo endoscope system is described. FIG. 3 shows an optical arrangement of a stereo endoscope intended to be connected to a stereo camera head, which includes an objective optical system pair (OBSP), a relay optical system or a relay optical system pair (RSP), an imaging optical system pair (ISP), and an ocular optical system pair (OCSP). Images formed by the objective optical system pair (OBSP) are transferred by the relay optical system pair (RSP) having two optical axes. Preferably, one of the imaging optical system pair (ISP) or the ocular optical system pair (OCSP) incorporates the stereo optical system pair according to the three structures described earlier. Magnification matching error caused by the objective optical system pair (OBSP), the relay optical system pair (RSP), the imaging optical system pair (ISP), the ocular optical system pair (OCSP) may be adjusted by the stereo optical system pair. In alternative structure, images formed by the objective optical system pair (OBSP) are transferred by the relay optical system having only one optical axis (not shown in FIG. 3). In such an arrangement, the magnification matching error caused by the relay optical system will generally be negligible. According to above constitution, magnification matching in the endoscope can be easily realized.

In the arrangement of FIG. 3, it is less preferable to incorporate the stereo optical system pair in the objective optical system pair (OBSP) because the objective optical system pair is typically assembled first. Adjustment of stereo matching properties is preferably the final procedure of assembling the system.

Figure 4:
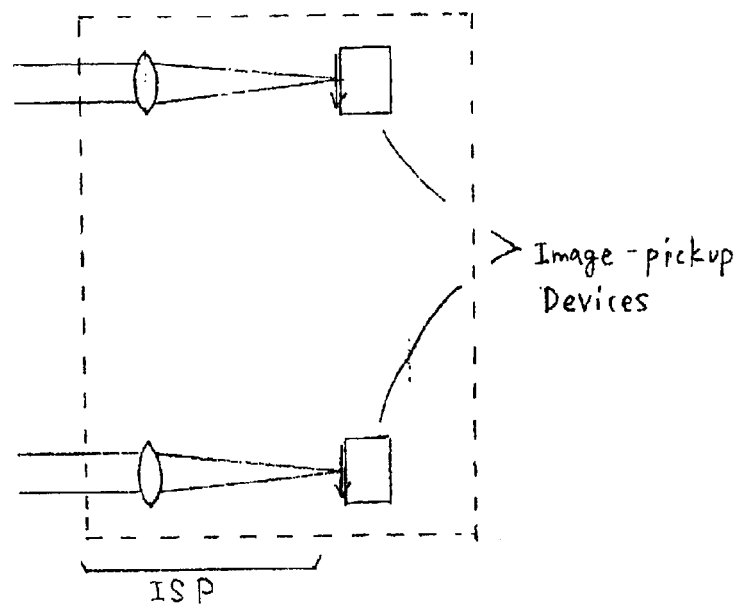
FIG. 4 is a diagram showing an arrangement of a stereo optical system pair according to an embodiment of this invention in a stereo camera head to be connected to a stereo endoscope.

FIG. 4 shows an optical arrangement of a stereo camera head intended to be connected to a stereo endoscope, which includes an imaging optical system pair (ISP) incorporating the stereo optical system pair according to the three structures described earlier. In this arrangement, magnification matching error is caused by the imaging optical system pair (ISP) alone, and adjustment is made by adjusting the ISP itself.

Figure 5:
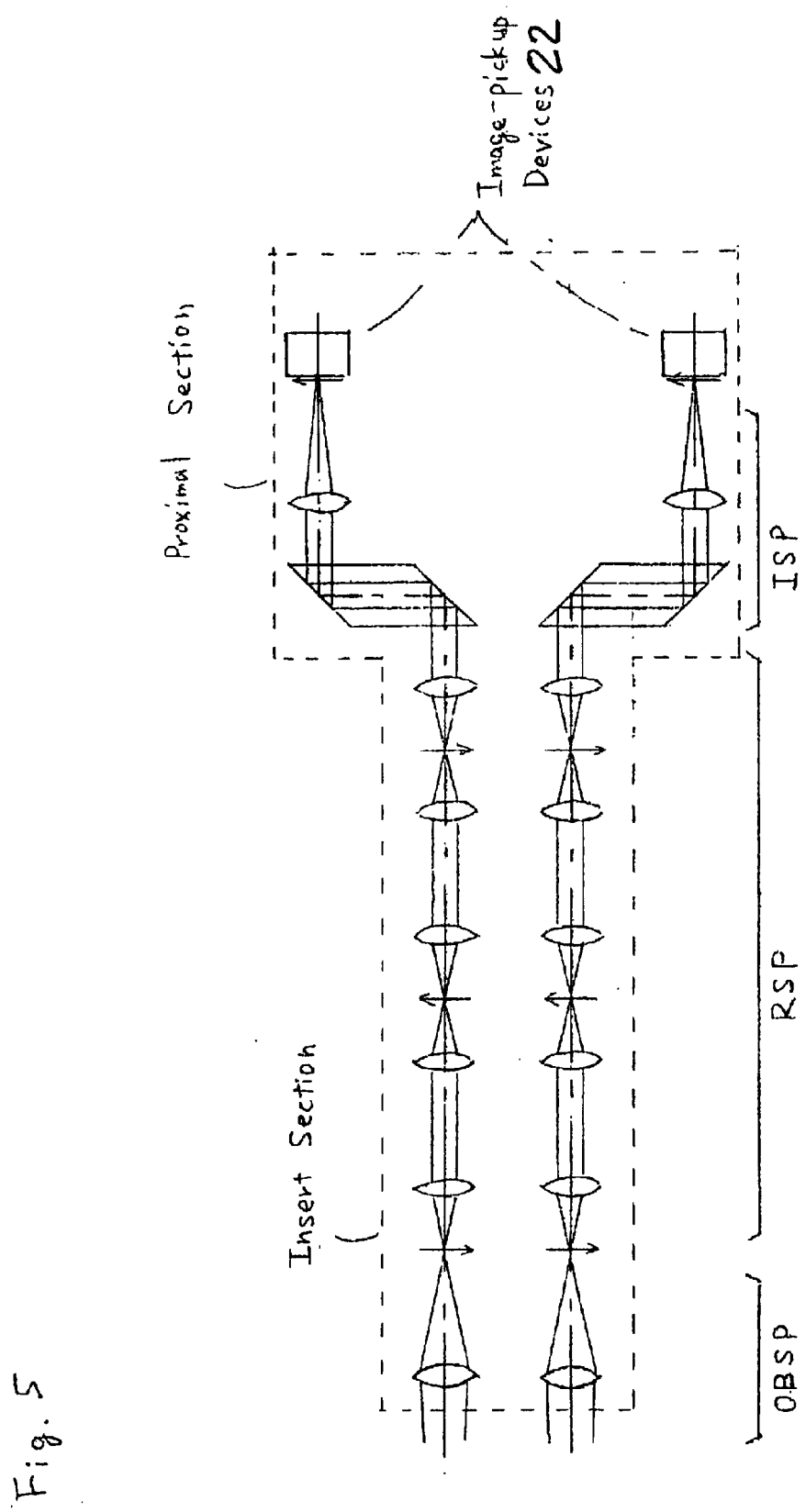
FIG. 5 is a diagram showing an arrangement of a stereo optical system pair according to an embodiment of this invention in a stereo endoscope which has image-pickup devices near a proximal end.

FIG. 5 shows an optical arrangement of a stereo endoscope intended to be used with image-pickup devices near the proximal end, which includes an objective optical system pair (OBSP), a relay optical system or a relay optical system pair (RSP), and an imaging optical system pair (ISP). Images formed by the imaging optical system pair (ISP) are detected by a pair of image-pickup devices 22, respectively. The imaging optical system pair incorporates the stereo optical system pair according to the three structures described earlier.

The adjustment for this arrangement is similar to that for the arrangement shown in FIG. 3. Magnification matching error caused by the objective optical system pair (OBSP), the relay optical system pair (RSP), and the imaging optical system pair (ISP) may be adjusted by the imaging optical system pair (ISP).

Figure 6:
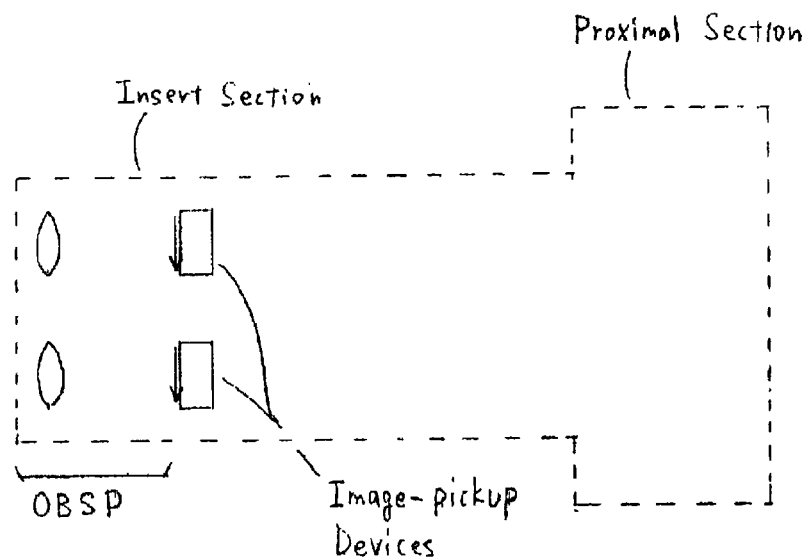
FIG. 6 is a diagram showing an arrangement of a stereo optical system pair according to an embodiment of this invention in a stereo endoscope which has image-pickup devices near a distal end.

FIG. 6 shows an optical arrangement of a stereo endoscope intended to be used with image-pickup devices near the distal end, which includes an objective optical system pair (OBSP) incorporating the stereo optical system pair according to the three structures described earlier. In this arrangement, magnification matching error is caused by the objective optical system pair (OBSP) alone, and adjustment is made by adjusting the OBSP itself.

Stereo optical system pair structures for a stereo endoscope have been described above according to embodiments of the present invention. It will be apparent to those skilled ill the art that various modification and variations can be made in the embodiments of the present invention without departing from the spirit or scope of the invention. Thus, it is intended that the present invention cover modifications and variations that come within the scope of the appended claims and their equivalents.

What is claimed is:

1. A stereo optical system pair for a stereo endoscope system, comprising:
    a right optical system and a left optical system, each of which includes a lens group which has a refractive power;
    wherein only one of the right and left optical systems includes a lens group that is moveable axially for magnification adjustment with a moveable range and has a position within the moveable range at which its optical magnification equals to −1.

2. The stereo optical system pair of claim 1,
    wherein the right and left optical systems includes, in the order from a far conjugation side, a first lens group which has a negative refractive power, and a second lens group, which has a positive refractive power, and
    wherein the moveable lens group is the second lens group, which is moveable axially independently from the first lens group.

3. The stereo optical system pair of claim 1,
    wherein the right and left optical systems includes, in the order from a far conjugation side, a first lens group which has a positive refractive power, a second lens group, which has a negative refractive power, and a third lens group which has positive refractive power, and
    wherein the moveable lens group is the second lens group, which is moveable axially independently from the first and third lens groups.

4. An objective optical system pair for a stereo endoscope system, comprising:
    a right optical system and a left optical system,
    wherein one of the right and left optical systems includes, in the order from a far conjugation side, a first lens group which has a positive refractive power, a second lens group which has a negative refractive power, and a third lens group which has a positive refractive power, and
    wherein the second lens group is moveable axially independently from the first and third lens groups with a moveable range and has a position within the moveable range at which its optical magnification equals to −1.

5. A stereo optical system pair for a stereo endoscope system, comprising:
    a right optical system and a left optical system, each of which includes a lens group which has a refractive power,
    wherein only one of the right and left optical systems includes a lens group that is axially moveable for magnification adjustment with a moveable range and has a position within the moveable range at which its optical magnification equals to the value which is selected within the range of −1.2 to −0.8.

6. The stereo optical system pair of claim 5,
    wherein the right and left optical systems include, in the order from a far conjugation side, a first lens group which has a negative refractive power, and a second lens group which has a positive refractive power,
    wherein the moveable lens group is the second lens group which is moveable axially independently from the first lens group.

7. The stereo optical system pair of claim 5,
    wherein the right and left optical systems include, in the order from a far conjugation side, a first lens group which has a positive refractive power, a second lens group which has a negative refractive power, and a third lens group which has a positive refractive power,
    wherein the moveable lens group is the second lens group which is moveable axially independently from the first and third lens groups.

8. An objective optical system pair for a stereo endoscope system, comprising:
    a right optical system and a left optical system;
    wherein one of the right and left optical systems includes, in the order from a far conjugation side, a first lens group which has a positive refractive power, a second lens group which has negative refractive power, and a third lens group which has positive refractive power, and
    wherein the second lens group is moveable axially independently from the first and third lens groups with a moveable range and has a position within the moveable range at which its optical magnification equals to the value which is selected within the range of −0.8 to −1.2.

9. The stereo optical system pair of claim 2,
wherein the second lens group is moveable only in a production process.

10. An optical system for stereo endoscope including the stereo optical system pair of claim 9, the optical system comprising:
an objective optical system pair;
a relay optical system;
an imaging optical system pair; and
an ocular optical system pair,
wherein only one of the imaging optical system pair and the ocular optical system pair is the stereo optical system pair.

11. An optical system for stereo endoscope including the stereo optical system pair of claim 9, the optical system comprising:
an objective optical system pair;
a relay optical system; and
an imaging optical system pair,
wherein the imaging optical system pair is the stereo optical system pair.

12. An optical system for stereo endoscope including the stereo optical system pair of claim 9, the optical system comprising:
an objective optical system pair which is the stereo optical system pair.

13. The stereo optical system pair of claim 3,
wherein the second lens group is moveable only in a production process.

14. The stereo optical system pair of claim 6,
wherein the second lens group is moveable only in a production process.

15. The stereo optical system pair of claim 7,
wherein the second lens group is moveable only in a production process.

16. An optical system for stereo endoscope including the stereo optical system pair of claim 13, optical system comprising:
an objective optical system pair;
a relay optical system;
an imaging optical system pair; and
an ocular optical system pair,
wherein only one of the imaging optical system pair and the ocular optical system pair is the stereo optical system pair.

17. An optical system for stereo endoscope including the stereo optical system pair of claim 5, the optical system comprising:
an objective optical system pair;
a relay optical system;
an imaging optical system pair; and
an ocular optical system pair,
wherein only one of the imaging optical system pair and the ocular optical system pair is the stereo optical system pair.

18. An optical system for stereo endoscope including the stereo optical system pair of claim 6, the optical system comprising:
an objective optical system pair;
a relay optical system;
an imaging optical system pair; and
an ocular optical system pair,
wherein only one of the imaging optical system pair and the ocular optical system pair is the stereo optical system pair.

19. An optical system for stereo endoscope including the stereo optical system pair of claim 13, the optical system comprising:
an objective optical system pair;
a relay optical system; and
an imaging optical system pair,
wherein the imaging optical system pair is the stereo optical system pair.

20. An optical system for stereo endoscope including the stereo optical system pair of claim 5, the optical system comprising:
an object optical system pair;
a relay optical system; and
an imaging optical system pair,
wherein the imaging optical system pair is the stereo optical system pair.

21. An optical system for stereo endoscope including the stereo optical system pair of claim 6, the optical system comprising:
an objective optical system pair;
a relay optical system; and
an imaging optical system pair,
wherein the imaging optical system pair is the stereo optical system pair.

22. An optical system for stereo endoscope inducting the stereo optical system pair of claim 13, the optical system comprising:
an objective optical system pair which is the stereo optical system pair.

23. An optical system for stereo endoscope including the stereo optical system pair of claim 5, the optical system comprising:
an objective optical system pair which is the stereo optical system pair.

24. An optical system for stereo endoscope including the stereo optical system pair of claim 6, the optical system comprising:
an objective optical system pair which is the stereo optical system pair.

25. An optical system for stereo camera head including the stereo optical system pair of claim 9, comprising:
an imaging optical system pair which is the stereo optical system pair.

26. An optical system for stereo camera head including the stereo optical system pair of claim 13, comprising:
an imaging optical system pair which is the stereo optical system pair.

27. An optical system for stereo camera head including the stereo optical system pair of claim 5, comprising:
an imaging optical system pair which is the stereo optical system pair.

28. An optical system for stereo camera head including the stereo optical system pair of claim 6, comprising:
an imaging optical system pair which is the stereo optical system pair.

* * * * *